(12) United States Patent
Miura et al.

(10) Patent No.: US 8,957,248 B2
(45) Date of Patent: Feb. 17, 2015

(54) PROCESS FOR PRODUCING ACETIC ACID

(75) Inventors: Hiroyuki Miura, Himeji (JP);
Masahiko Shimizu, Tokyo (JP);
Takashi Ueno, Himeji (JP); Kazuo Yamaguchi, Osaka (JP); Kensuke Goto, Otake (JP)

(73) Assignee: Daicel Corporation, Osaka-Shi (JP)

( * ) Notice: Subject to any disclaimer, the term of this patent is extended or adjusted under 35 U.S.C. 154(b) by 0 days.

(21) Appl. No.: 13/806,290

(22) PCT Filed: Jul. 11, 2011

(86) PCT No.: PCT/JP2011/003971
§ 371 (c)(1),
(2), (4) Date: Dec. 21, 2012

(87) PCT Pub. No.: WO2012/014393
PCT Pub. Date: Feb. 2, 2012

(65) Prior Publication Data
US 2013/0116470 A1   May 9, 2013

(30) Foreign Application Priority Data

Jul. 26, 2010   (JP) ................. 2010-167239

(51) Int. Cl.
*C07C 51/43* (2006.01)
*C07C 51/44* (2006.01)
*C07C 51/12* (2006.01)

(52) U.S. Cl.
CPC ............... *C07C 51/12* (2013.01); *C07C 51/43* (2013.01); *C07C 51/44* (2013.01)
USPC ........................................................ 562/519

(58) Field of Classification Search
CPC .................................................... C07C 51/12
See application file for complete search history.

(56) References Cited

U.S. PATENT DOCUMENTS

| 4,391,753 | A | 7/1983 | Hardy et al. |
| 5,374,774 | A | 12/1994 | Ochiai |
| 5,874,610 | A | 2/1999 | Clode et al. |
| 2006/0093535 | A1 | 5/2006 | Nakajima et al. |
| 2009/0036710 | A1 | 2/2009 | Miura et al. |

FOREIGN PATENT DOCUMENTS

| EP | 0 573 189 A1 | 12/1993 |
| JP | 54-160313 A | 12/1979 |
| JP | 06-040998 A | 2/1994 |
| JP | 06-040999 A | 2/1994 |
| JP | 06-321847 A | 11/1994 |
| JP | 09-040590 A | 2/1997 |
| JP | 2001-151715 A | 6/2001 |
| JP | 2002-255890 A | 9/2002 |
| JP | 3616400 B2 | 2/2005 |
| JP | 2006-160645 A | 6/2006 |
| WO | WO 02/068374 A1 | 9/2002 |

OTHER PUBLICATIONS

International Search Report for PCT/JP2011/003971 dated Dec. 14, 2011.
Written Opinion of the International Searching Authority for PCT/JP2011/003971 dated Dec. 14, 2011.
Forms PCT/IB/338, PCT/IB/373 and PCT/IB/237, for International Application No. PCT/JP2011/077845 mailed Jun. 27, 2013.
International Search Report for PCT/JP2011/077845 dated Apr. 17, 2012.
Machine Translation for JP 2001-151715 (patent published Jun. 5, 2001).
U.S. Office Action for U.S. Appl. No. 13/994,275, dated Feb. 21, 2014.
U.S. Office Action for U.S. Appl. No. 13/994,275, dated Sep. 11, 2014.

*Primary Examiner* — Brandon Fetterolf
*Assistant Examiner* — Ana Z Muresan
(74) *Attorney, Agent, or Firm* — Birch, Stewart, Kolasch & Birch, LLP (57) ABSTRACT

A production process of acetic acid comprises a reaction step for continuously allowing at least one member selected from the group consisting of methanol, dimethyl ether, and methyl acetate to react with carbon monoxide in a catalyst system comprising a rhodium catalyst, an iodide salt, and methyl iodide in the presence of acetic acid and water in a plant comprimising a reactor 1; a flasher 2; and a distillation column 3; wherein part of the vaporized stream is introduced into a heat exchanger 7. The process achieves a production of acetic acid with a high purity in a resource-saving and energy-saving equipment by efficiently removing a reaction heat even in a large-sized plant.

10 Claims, 1 Drawing Sheet

PROCESS FOR PRODUCING ACETIC ACID

TECHNICAL FIELD

The present invention relates to a process for producing acetic acid with a high purity in a resource-saving and energy-saving equipment in a large-sized plant.

BACKGROUND ART

In a plant for producing acetic acid using a methanol method, carbon monoxide is allowed to react with methanol in a carbonylation reactor, the reaction solution is vaporized by an evaporator (flasher), and the resulting vaporized product is further distilled by a distillation column for separation to produce acetic acid. Since such steps generates reaction heat due to the carbonylation reaction, it is necessary to remove the reaction heat. As a system for removing the reaction heat in this plant, a method of removing the reaction heat by utilizing a latent heat of evaporation of acetic acid generated in an evaporator and a latent heat of evaporation of constituents (e.g., methyl iodide, methyl acetate, water, and other by-products) of the reaction solution accompanying acetic acid evaporation is effective. In particular, this heat removal method is used according to the plant size and is effective in a conventional plant in which the amount of production per plant is about 200,000 t/year (a heating value of about $1.36 \times 10^7$ kcal/hour), and the heat removal method is economical in the respect that the flash amount necessary for separating and collecting acetic acid produced in the reactor is well-proportioned by excellent material balance and heat balance. In these years, however, the economical scale of the acetic acid production plant is increasing to an amount of production of not less than about 400,000 t/year per plant, one reason of which is the growth in demand. For the scale of an amount of production of not less than 250,000 t/year, it is necessary to remove the quantity of heat larger than the latent heat of evaporation of the produced acetic acid or the like. Thus, only the heat removal method utilizing the latent heat of evaporation is insufficient for removing the reaction heat.

Regarding a system for removing a reaction heat, U.S. Pat. No. 5,374,774 publication (Patent Document 1) discloses a method for controlling a liquid surface of a reactor and that of an evaporator in a process for producing acetic acid using a methanol method. In this document, as a method for controlling the temperature of the reactor, a method for providing a recycle line, for recycling a catalyst from a bottom solution of the evaporator to the reactor, with a cooling unit, and a method for providing the reactor with a cooler (a cooling unit) are described.

However, according to the method for providing the catalyst recycle line with the cooling unit, since sensible heat is used for the heat removal, it is necessary to install an expensive equipment using a high-grade material with a high corrosion resistance, and the amount of removed heat is small. Moreover, according to the method for providing the reactor with the cooling unit, since a reaction solution as well as the reactor is exposed to a high temperature and a high pressure, carbon monoxide dissolved in the reaction solution is consumed in pipelines. Thus, it is difficult to maintain an active state of a rhodium-carbonyl complex as an active catalyst species (for example, $[RhI_2(CO)_2]^-$, $[RhI_2(CO)_4]^-$). The main catalyst Rh does not contribute to the reaction due to sedimentation thereof, e.g., in the state of $RhI_3$, or the sediment blockades the pipeline or the like and causes incomplete actions of a valve, a pump, or the like, and it is difficult to operate the system stably. Further, the method requires use of a high-grade material with a high corrosion resistance. However, the equipment for the use under a high temperature and a high pressure is expensive, and the reaction solution is easy to leak. Thus, it is difficult to operate the system stably.

Moreover, Japanese Patent No. 3616400 publication (JP-3616400B, Patent Document 2) discloses a process for purifying an acetic acid product using a single distillation column, which comprises operating a liquid-phase carbonylation reaction by controlling a formulation thereof. This document discloses that the loss due to evaporation during the process is minimalized by cooling a vapor from a flash tank and a non-condensation product from the head of the distillation column. Specifically, in a series of steps for recycling the cooled condensate to a reaction vessel, most of the quantity of heat of the reaction solution withdrawn from the reaction vessel is transferred as the quantity of heat of a flash vapor and removed by condensing the flash vapor in a condenser installed to the top of the distillation column.

However, in the method for removing heat by the condenser installed to the top of the distillation column, the condenser is subjected to a large load, and the cost of equipment or the energy cost is so large that it can no more be disregarded. In particular, for the recent large-sized plant, the size of the condenser and that of the distillation column have to be increased.

Further, Japanese Patent Application Laid-Open No. 2002-255890 (JP-2002-255890A, Patent Document 3) discloses a method for controlling a temperature of a reaction system by controlling a quantity of heat according to a circulation amount of a separated component which is separated in a step for separating a reaction product. In the method, the quantity of heat is controlled by installing a temperature control unit (a heat exchanger) and a control unit in a circulation line for returning a higher boiling point component separated in a flash distillation column to the reaction system.

This method is effective in stably operating the system. However, for a large-sized plant, only cooling of the liquid (sensible heat) is insufficient to remove the heat.

CITATION LIST

Patent Literature

PTL 1: U.S. Pat. No. 5,374,774 publication (Claims and Column 7, lines 48 to 66)
PTL 2: JP-3616400B (Claims and Examples)
PTL 3: JP-2002-255890A (Claims, Paragraphs [0021] to [0023], and Examples)

SUMMARY OF INVENTION

Problems to be Solved by the Invention

It is therefore an object of the present invention to provide a process for producing acetic acid with a high yield and a high purity, the process inhibiting a loss of carbon monoxide in a resource-saving and energy-saving equipment having a miniaturized (or downsized) apparatus (e.g., a distillation column) even for a large-sized plant.

It is another object of the present invention to provide a method for controlling a temperature efficiently and accurately in a production process of acetic acid.

Means to Solve the Problems

The inventors of the present invention made intensive studies to achieve the above objects and finally found that, in a process for producing acetic acid with a high purity continuously by allowing at least one member selected from the group consisting of methanol, dimethyl ether, and methyl acetate to react with carbon monoxide, a loss of carbon monoxide in a resource-saving and energy-saving equipment having a miniaturized apparatus (e.g., a distillation column) even for a large-sized plant can be inhibited by introducing part of a vaporized stream (or a vapor product or a lower boiling point fraction) withdrawn from a flasher into a heat exchanger, condensing the introduced vaporized stream and recycling the condensed stream (or fraction) to the reactor, and acetic acid with a high purity can be produced with a high yield. The present invention was accomplished based on the above findings.

That is, the process for producing acetic acid according to the present invention comprises a reaction step for continuously allowing at least one member selected from the group consisting of methanol, dimethyl ether, and methyl acetate to react with carbon monoxide in a catalyst system comprising a rhodium catalyst, an iodide salt, and methyl iodide in the presence of acetic acid and water in a reactor; a flash evaporation step for continuously feeding a flasher with a liquid reaction medium (or a reaction mixture) withdrawn from the reactor to separate a liquid stream (or a higher boiling point fraction) and a vaporized stream (or a lower boiling point fraction) from the liquid reaction medium; and a distillation step for feeding a distillation column with the vaporized stream for obtaining a purified acetic acid; wherein part of the vaporized stream is introduced into a heat exchanger for condensation, and a liquefied stream (or liquid fraction) condensed by the heat exchanger is recycled to the reactor. Into the heat exchanger, 1 to 50% by weight of the vaporized stream may be introduced. Moreover, an acetic acid stream obtained from the distillation step for purifying acetic acid may be subjected to a further distillation and/or adsorption treatment for obtaining a further purified acetic acid. In the process of the present invention, a further heat removal method may be used in combination. For example, the process may be used in combination with a manner in which the liquid stream separated by the flasher is introduced into the heat exchanger and cooled, and then the cooled stream is recycled to the reactor; or a manner in which each of a gaseous component (or a lower boiling point fraction) from the reactor and an overhead fraction (or a lower boiling point fraction) from the distillation column(s) is condensed by a condenser. In the process of the present invention, the reactor may be a reactor without a heat-removable (or heat-removing) or cooling unit. In the reaction step, the reaction may be conducted while maintaining the reaction system at concentrations of the iodide salt of 2 to 25% by weight (particularly, 6 to 25% by weight), methyl iodide of 1 to 20% by weight, methyl acetate of 0.1 to 30% by weight, and water of 0.1 to 10% by weight (particularly, 0.1 to 6% by weight) in a whole liquid phase of the reaction system.

The present invention also includes a method for controlling a temperature in a production process of acetic acid, which comprises a reaction step for continuously allowing at least one member selected from the group consisting of methanol, dimethyl ether, and methyl acetate to react with carbon monoxide in a catalyst system comprising a rhodium catalyst, an iodide salt, and methyl iodide in the presence of acetic acid and water; a flash evaporation step for continuously withdrawing a liquid reaction medium from the reaction step to separate a liquid stream and a vaporized stream (or vapor product) from the liquid reaction medium; and a distillation step for distilling the vaporized stream for obtaining a purified acetic acid; wherein part of the vaporized stream is introduced into a heat exchanger for condensation, and a liquefied stream (or liquid fraction) condensed by the heat exchanger is recycled to the reaction step.

This method is advantageous to a temperature control in a system in which the fluctuation (or change) of the pressure and/or flow rate is transmitted to the succeeding step(s) or influences the succeeding step(s). Incidentally, depending on the temperature fluctuation, the absorption efficiency of the carbon monoxide fed under pressure also fluctuates, and the pressure fluctuation is caused. Thus, the temperature fluctuation interferes with the effective utilization of carbon monoxide and has a disadvantage for energy efficiency. According to the method of the present invention, since the temperature fluctuation is controlled, the control of the pressure fluctuation and the effective utilization of carbon monoxide are achieved. Thus, the method of the present invention also refers to a method for saving a resource (e.g., carbon monoxide) and an energy while inhibiting the decrease of the yield and purity of acetic acid.

Effect of the Invention

According to the present invention, in a process for producing acetic acid with a high purity by allowing at least one member selected from the group consisting of methanol, dimethyl ether, and methyl acetate to continuously react with carbon monoxide, since part of the vaporized stream withdrawn from a flasher is introduced into the heat exchanger and condensed to recycle the condensed fraction to the reactor, part of the quantity of heat transferred from the reaction solution to the flash vapor can be removed before heat removal utilizing a latent heat of evaporation in the distillation column even for a large-sized plant, it is unnecessary to install a cooling unit in the reactor, and carbon monoxide dissolved in the reaction solution can be utilized effectively. Thus, even for a large-sized plant, the loss of carbon monoxide can be inhibited in a resource-saving and energy-saving equipment having a miniaturized apparatus (e.g., a distillation column), and acetic acid with a high purity can be produced with a high yield.

DETAILED DESCRIPTION OF THE INVENTION

Figure 1:
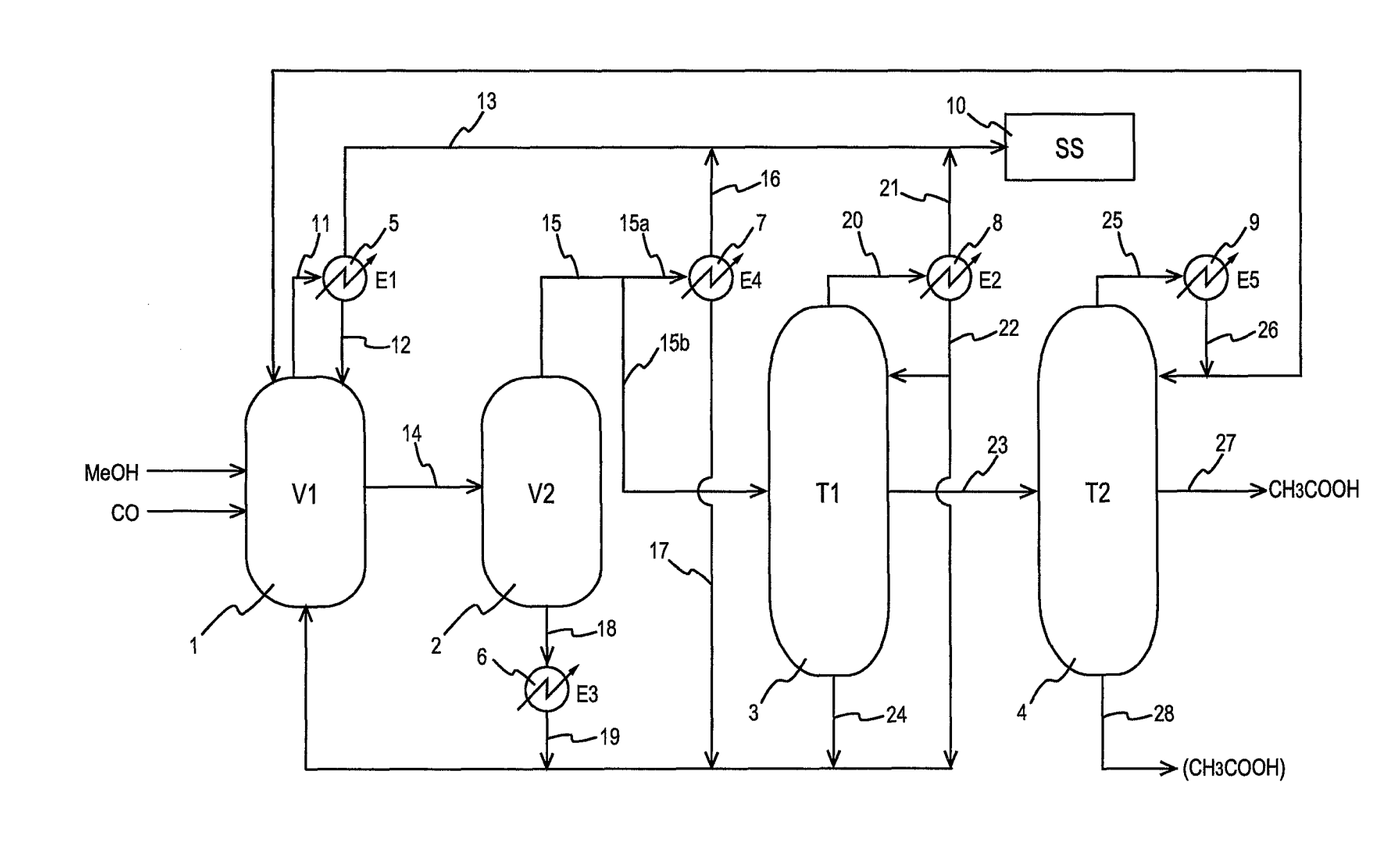
FIG. 1 is a diagram for explaining a production process of acetic acid in accordance with an embodiment of the present invention.

Hereinafter, the present invention will be explained in detail with reference to the drawings. FIG. 1 is a diagram (a flow sheet, a schematic process drawing, or a schematic plant layout drawing) for explaining a production process of acetic acid in accordance with an embodiment of the present invention.

The embodiment of FIG. 1 shows a process for producing a purified acetic acid from a liquid reaction medium generated by a continuous carbonylation reaction of methanol with carbon monoxide in a liquid-phase system in the presence of a carbonylation catalyst system comprising a rhodium catalyst and a co-catalyst (lithium iodide and methyl iodide), as well as acetic acid, methyl acetate, and a finite amount of water.

The process comprises a reactor (reaction system) 1 for carrying out the above-mentioned carbonylation reaction of methanol; a flasher (flash distillation column) 2 for separating a liquid stream (or a higher boiling point fraction) mainly containing a metal catalyst component (a higher boiling point component) (e.g., a rhodium catalyst and lithium iodide) and an acetic acid stream (a vaporized stream or a lower boiling point fraction) from a liquid reaction medium (or a reaction mixture or a reaction solution) which is introduced through a feed line 14 and contains acetic acid generated by the reaction; a first distillation column 3 for removing at least part of a first overhead fraction (or a lower boiling point fraction) containing a lower boiling point component (e.g., methyl iodide, methyl acetate, and acetaldehyde) out of the acetic acid stream introduced from the flasher 2 through feed lines 15 and 15b as an overhead from a column top thereof and withdrawing an acetic acid stream from a side stream by side cut; a second distillation column 4 for removing at least part of a second overhead fraction (or a lower boiling point fraction) containing a lower boiling point component as an overhead from a column top thereof out of the acetic acid stream introduced from the first distillation column 3 through a feed line 23 by side cut, separating at least part of a higher boiling point component (higher boiling point impurities) (e.g., propionic acid) from a bottom of the column, and obtaining an acetic acid stream through a feed line 27 from a side stream by side cut. The acetic acid stream obtained through a line 28 may be recycled to the reactor, may partly be abandoned, or may be used as a final product. If necessary, the acetic acid stream may be treated with flash and/or distillation, ion exchange resin, or adsorption.

Further, in this process, the reactor 1 is equipped with a condenser 5 for condensing a condensable component in a gaseous offgas discharged through a discharge line 11; a recycle line 12 for recycling a liquid component condensed by the condenser 5 to the reactor 1; and a discharge line 13 for discharging a gaseous component, which is a non-condensed component in the condenser 5.

In this process, the flasher 2 is equipped with a heat exchanger 6 for cooling a liquid stream separated by the flasher 2 and discharged from the bottom of the flasher 2 through a discharge line 18; a recycle line 19 for recycling the liquid stream cooled by the heat exchanger 6 to the reactor 1; a heat exchanger 7 for condensing a condensable component in part of the vaporized stream discharged from the top of the flasher 2 and introduced through the feed lines 15 and 15a; a discharge line 16 for discharging a gaseous component, which is a non-condensable component in the heat exchanger 7; and a recycle line 17 for recycling a liquid (or liquefied) component containing acetic acid condensed by the heat exchanger 7 to the reactor 1.

In this process, the first distillation column 3 is equipped with a condenser 8 for condensing a condensable component in the first overhead fraction discharged through a discharge line 20; a recycle line 22 for recycling a liquid component condensed by the condenser 8 to the first distillation column 3 and/or the reactor 1; and a discharge line 21 for discharging a gaseous component, which is a non-condensable component in the condenser 8.

In this process, the second distillation column 4 is equipped with a condenser 9 for condensing a condensable component in the second overhead fraction discharged through a discharge line 25; a recycle line 26 for recycling a liquid component condensed by the condenser 9 to the second distillation column 4 and/or the reactor 1; and a discharge line for discharging a gaseous component, which is a non-condensable component in the condenser 9.

This process comprises a scrubber system 10 for recovering methyl iodide and others as a valuable component contained in the gaseous components discharged from the condenser 5, the heat exchanger 7, and the condenser 8 and recycling the valuable component to the reactor 1. Incidentally, a line for recycling the valuable component from the scrubber system 10 to the reactor 1 is omitted in FIG. 1.

More specifically, methanol as a liquid component and carbon monoxide as a gaseous reactant may be continuously fed to the reactor 1 at a predetermined rate, and a catalyst mixture (a liquid catalyst mixture) containing a carbonylation catalyst system [a catalyst system comprising a main catalyst component (e.g., a rhodium catalyst) and a co-catalyst (e.g., lithium iodide and methyl iodide)] and water may be continuously fed to the reactor 1. Moreover, fraction(s) (e.g., in the form of liquid) containing lower boiling point fraction(s) and/or higher boiling point fraction(s) from the succeeding step(s) (e.g., the flasher 2, the first and second distillation columns 3 and 4, the heat exchanger 7, and the scrubber system 10) may be fed to the reactor 1. Then, inside the reactor 1, a liquid-phase reaction system containing the reactant and the higher boiling point component such as the metal catalyst component (e.g., a rhodium catalyst and lithium iodide) is in equilibrium with a vapor-phase system comprising carbon monoxide, by-products by the reaction (hydrogen, methane, carbon dioxide), and a partly vaporized lower boiling point component (e.g., methyl iodide, acetic acid as a product, and methyl acetate), and a carbonylation reaction of methanol proceeds under stirring by a stirrer or other means. The inner pressure of the reactor 1 (e.g., reaction pressure, carbon monoxide partial pressure, and hydrogen partial pressure) may be maintained constantly by withdrawing a vapor from the upper part (or column top) and introducing the withdrawn vapor into the condenser 5. The introduced vapor is cooled by the condenser 5 to give a liquid component (containing acetic acid, methyl acetate, methyl iodide, acetaldehyde, water, and others) and a gaseous component (containing carbon monoxide, hydrogen, and others). The resulting liquid component is recycled to the reactor 1, and the resulting gaseous component (waste gas) is fed to the scrubber system 10. A valuable component (e.g., methyl iodide) is recovered by the scrubber system 10 to be recycled to the reactor 1. In particular, the reaction system is an exothermic reaction system that accompanies heat generation, and part of the quantity of heat generated in the reactor may be removed by cooling part of the reaction heat transferred from the reaction solution to the vapor with the condenser 5.

To the reactor 1, if necessary, hydrogen may be fed in order to increase the catalytic activity. Moreover, since the reaction system is an exothermic reaction system that accompanies heat generation, the reactor 1 may be equipped with a heat-removable (or heat-removing) or cooling unit (e.g., a jacket) for controlling a reaction temperature. According to the present invention, the heat can be removed without the heat-removing or cooling unit. Thus, effective use of carbon monoxide and inhibition of decrease in the rhodium catalyst activity result in improvement of the reaction efficiency.

Components contained in the reaction mixture (crude reaction solution) generated in the reactor 1 may include acetic acid, hydrogen iodide, a lower boiling point component or lower boiling point impurity having a boiling point lower than that of acetic acid (e.g., methyl iodide as a co-catalyst, methyl acetate as a reaction product of acetic acid with methanol, and acetaldehyde, a higher iodide (such as hexyl iodide or decyl iodide) as by-products), and a higher boiling point component or higher boiling point impurity having a boiling point higher than that of acetic acid [a metal catalyst component (a rhodium catalyst, and lithium iodide as a co-catalyst), propionic acid, and water].

In order to mainly separate the higher boiling point component (such as the metal catalyst component) from the reaction mixture, part of the reaction mixture is continuously withdrawn from the reactor 1 and introduced or fed into the flasher 2. In the flasher 2, from the reaction mixture, a liquid stream (mainly containing a metal catalyst component, e.g., a rhodium catalyst, lithium iodide, and others), and a vaporized stream (mainly containing acetic acid which is a product and also functions as a reaction solvent, methyl acetate, methyl iodide, water, hydrogen iodide, and others) are separated, and the liquid stream is withdrawn from the bottom of the flasher and introduced into the heat exchanger 6. Also in this step, part of the reaction heat is removed by cooling the liquid stream with the heat exchanger 6. Incidentally, in the liquid stream, the metal catalyst component, and in addition, components remaining without evaporation (e.g., methyl iodide, methyl acetate, hydrogen iodide, water, and acetic acid) are also contained.

On the other hand, the vaporized stream (acetic acid stream) is withdrawn from the column top or upper part of the flasher 2 and fed or introduced into the first distillation column 3, and part of the vaporized stream is introduced into the heat exchanger 7 to be condensed. Specifically, the introduced stream is cooled by the heat exchanger 7 to produce a liquid component (acetic acid, methyl iodide, methyl acetate, water, and propionic acid) and a gaseous component (containing carbon monoxide, hydrogen, and others). The resulting liquid component is recycled to the reactor 1. The resulting gaseous component (waste gas) is fed to the scrubber system 10, and methyl iodide and others are recovered. The recovered matter is then recycled to the reactor 1. Moreover, differently from the process shown in FIG. 1, instead of recycling of the liquid component to the reactor 1, the liquid component may be purified with the after-mentioned distillation and/or adsorption treatment or other means to give acetic acid with a high purity. According to the present invention, the vaporized stream is withdrawn from the flasher to introduce into the heat exchanger, and part of the reaction heat transferred from the reaction solution to the flash vapor is cooled and removed by the heat exchanger. Accordingly, the heat can efficiently be removed. Thus, according to the present invention, since the size of the succeeding distillation column or condenser can be miniaturized even for a large-sized plant, acetic acid can be produced with a high purity and a high yield in a resource-saving and energy-saving equipment. Further, the heat can be removed without installing an external circulation cooling unit in the reactor, which leads to the prevention of carbon monoxide loss and the improvement of the reaction efficiency or the cost reduction of equipment. That is, according to the conventional method which comprises transferring the reaction heat to the flash vapor and removing the reaction heat by condensing the flash vapor in the condenser installed to the top of the distillation column, it is necessary to remove the quantity of heat which largely surpass the quantity of heat needed to vaporize acetic acid produced in the reactor from the reaction solution. Thus it is necessary that the condenser and the distillation column be far larger in size than the equipment necessary for purifying acetic acid, and the energy cost is increased. Moreover, when the reactor provided with a cooling unit is used, the reaction solution is exposed to a high temperature and a high pressure in a line or pipeline (or a line for feeding the reaction solution to the cooling unit and a line installed in the cooling unit) until the temperature of the reaction solution is decreased by the cooling unit. Thus, acetic acid is produced in the line as well as the reactor, carbon monoxide is consumed in the line, and the rhodium catalyst is precipitated. In contrast, according to the present invention, in a production process of acetic acid without the use of a cooling unit the temperature can be controlled efficiently and accurately by previously removing the quantity of heat unnecessary for the purification of acetic acid with a heat-exchanger, and the problems are solved.

Incidentally, by making (keeping) the inner temperature and/or pressure of the flasher 2 lower than those of the reactor 1, further generation of by-products or deterioration of the catalytic activity may be inhibited.

In the first distillation column 3, usually, a first overhead fraction (or a lower boiling point fraction) containing part of the lower boiling point component (containing methyl iodide, methyl acetate, acetaldehyde, water, and others) is separated from the top or upper part of the column and fed to the condenser 8, and a first bottom fraction (or a higher boiling point fraction) containing the higher boiling point component (e.g., water, and propionic acid) is separated from the bottom or lower part of the column through a bottom line and recycled to the reactor 1 or the flasher 2. Further, a side stream (acetic acid stream) mainly containing acetic acid is withdrawn from the first distillation column 3 by side cut and is fed or introduced into the second distillation column 4.

The first overhead fraction withdrawn from the top or upper part of the first distillation column 3 contains acetic acid and others, and is fed to the condenser 8. In the condenser 8, the first overhead fraction is condensed to separate a gaseous component mainly containing carbon monoxide, hydrogen and others, and a liquid component containing methyl iodide, methyl acetate, acetic acid, water, acetaldehyde and others. The gaseous component separated in the condenser 8 is fed to the scrubber system 10 to recover methyl iodide and others, and the recovered matter is recycled to the reaction system 1 (not shown). The liquid component separated in the condenser 8 may be recycled to the first distillation column 3. Moreover, for the liquid component containing a predetermined amount of water, differently from the process shown in FIG. 1, the liquid component may be separated into an aqueous phase and an oily phase, and the oily phase, which contains a large amount of methyl iodide as a co-catalyst, may be recycled to the reactor 1, and the aqueous phase, which contains large amounts of methyl acetate, acetic acid, acetaldehyde, and others, may be recycled to the first distillation column 3. In contrast, the aqueous phase may be recycled to the reactor 1 and the oily phase may be recycled to the first distillation column 3; or the aqueous phase and the oily phase may be partly mixed and the mixture may be recycled to the reactor 1 or the first distillation column 3. In the present invention, since the first overhead fraction withdrawn from the first distillation column 3 is condensed by the condenser 8, part of the reaction heat transferred from the reaction solution to the first overhead fraction through the flash vapor can be cooled by the condenser 8 and removed.

The first bottom fraction discharged from the bottom of the first distillation column 3 contains the higher boiling point component, as well as the lower boiling point component which remains without evaporation, acetic acid, and others, and is recycled to the reaction system 1. Incidentally, differently from the process shown in FIG. 1, the first bottom fraction may be recycled to the reactor 1 through the flasher 2.

In the acetic acid stream which is obtained by side cut from the first distillation column 3 and is fed to the second distillation column 4, at least part of the lower boiling point component (e.g., methyl iodide, methyl acetate, acetaldehyde, and water) remaining in the acetic acid stream is further separated in the second distillation column 4, and an acetic acid stream having a higher purity is withdrawn as a side stream. In the second distillation column 4, a second overhead fraction (or a lower boiling point fraction) containing the lower boiling point component is fed from the top or upper part of the column to the condenser 9, and a side stream (acetic acid stream) rich in acetic acid is distilled by side cut. If necessary, the second overhead fraction discharged from the top or upper part of the column may be recycled to the second distillation column 4 and/or the reaction system 1. Incidentally, a second bottom fraction (or a higher boiling point fraction) such as a higher boiling point component (e.g., propionic acid and iodide salt) may be discharged from the bottom of the column, and if necessary, may be recycled to the reactor 1 or may partly be wasted. Moreover, an acetic acid stream discharged from the bottom of the column without side cut may further be purified.

The second overhead fraction withdrawn from the top or upper part of the second distillation column 4 is condensed by the condenser 9 and is separated into a gaseous component mainly containing nitrogen or carbon monoxide, hydrogen, and others, and a liquid component containing acetic acid, methyl iodide, methyl acetate, water, acetaldehyde, and others. The gaseous component separated in the condenser 9 is recycled to the reactor 1. The liquid component separated in the condenser 9 may be recycled to the second distillation column 4. Moreover, for the liquid component containing a predetermined amount of water, in the same manner as in the first distillation column, the liquid component may be separated into an aqueous phase and an oily phase, and these phases may be recycled.

In this way, the production process of the present invention comprises a reaction step for continuously allowing methanol to react with carbon monoxide in a reactor; a flash evaporation step for continuously feeding a flasher with a liquid reaction medium (or a reaction mixture) withdrawn from the reactor to separate a liquid stream and a vaporized stream from the liquid reaction medium; and a distillation step for feeding a distillation column with the stream vaporized by the flasher to distill acetic acid; and in the process, the heat of the reaction (or the reaction heat) is removed, for example, by a step for introducing part of the vaporized stream into a heat exchanger and condensing the introduced stream.

(Reaction Step)

In the reaction step (carbonylation reaction system), at least one member selected from the group consisting of methanol, dimethyl ether, and methyl acetate (methanol and/or a derivative thereof) is carbonylated with carbon monoxide. Incidentally, methanol and/or a derivative thereof as a fresh raw material may be fed to the reaction system directly or indirectly, or methanol and/or a derivative thereof withdrawn from the distillation step may be recycled and fed to the reaction system.

The catalyst system in the reaction system may comprise a rhodium catalyst as a carbonylation catalyst, and a co-catalyst or an accelerator. The rhodium catalyst may be a rhodium as a simple substance or may be used in the form of an oxide (including a complex metal oxide), a hydroxide, a halide (e.g., a chloride, a bromide, and an iodide), a carboxylate (e.g., an acetate), a salt of an inorganic acid (e.g., a sulfate, a nitrate, and a phosphate), a complex, and others. Moreover, it is preferred to use the rhodium catalyst in the form dissolvable in a reaction solution. Incidentally, since rhodium usually exists as a complex in the reaction solution, the form of the catalyst is not particularly limited to a specific one as long as the catalyst can change into a complex in the reaction solution, and may be used in various forms. As such a rhodium catalyst, a rhodium iodide ($RhI_3$) or a rhodium complex (e.g., $[RhI_2(CO)_2]^-$ and $[RhI_2(CO)_4]^-$) is particularly preferred. Moreover, the catalyst may be stabilized in the reaction solution by addition of the after-mentioned iodide salt and/or water.

The concentration of the catalyst is, for example, about 200 to 3,000 ppm, preferably 300 to 2,000 ppm, and more preferably 500 to 1,500 ppm on the basis of weight in the whole liquid-phase system.

As the co-catalyst contained in the catalyst system, an iodide salt is used. The iodide salt may include, for example, an alkali metal iodide (e.g., lithium iodide, sodium iodide, potassium iodide, rubidium iodide, and cesium iodide), an alkaline earth metal iodide (e.g., beryllium iodide, magnesium iodide, and calcium iodide), an iodide of the group 3B metal of the Periodic Table (e.g., boron iodide and aluminum iodide), a phosphonium salt of an iodide (a phosphonium iodide) (e.g., tributylphosphine and triphenylphosphine), and an ammonium salt of an iodide (an ammonium iodide) (e.g., a salt of tertiary amine, a pyridine compound, an imidazole compound, or an imide compound with an iodide). These iodide salts may be used alone or in combination. Among these iodide salts, an alkali metal iodide (such as lithium iodide) is preferred.

The concentration of the iodide salt in the reaction system (reaction solution) in the reactor is, for example, about 2 to 30% by weight, preferably about 6 to 25% by weight, and more preferably about 7 to 25% by weight in the whole liquid phase of the reaction system. Further, the concentration of the iodide ion in the reaction system may be, for example, about 0.07 to 2.5 mol/liter and preferably 0.25 to 1.5 mol/liter.

As the accelerator contained in the catalyst system, an alkyl iodide (e.g., a $C_{1-4}$alkyl iodide such as methyl iodide, ethyl iodide, or propyl iodide, particularly methyl iodide, is utilized. The higher the concentration of the accelerator is, the more the reaction is accelerated (promoted). Thus, considering the recovery of the accelerator, an equipment size (or scale) for a circulating step of the recovered accelerator to the reactor, the amount of energy necessary for the recovery or circulation, and others, an economically advantageous concentration can suitably be selected. The concentration of the alkyl iodide (particularly, methyl iodide) in the reaction system is, for example, about 1 to 20% by weight, preferably about 5 to 20% by weight, and more preferably about 6 to 16% by weight in the whole liquid phase in the reaction system.

The reaction system may contain methyl acetate at a proportion of about 0.1 to 30% by weight, preferably about 0.5 to 20% by weight, and more preferably about 1 to 10% by weight in the whole reaction system. Incidentally, even when methanol or dimethyl ether is used as a raw material, methanol as the raw material exists in the reaction solution, and usually about 0.5 to 6% by weight of methyl acetate exists in the reaction solution in equilibrium with acetic acid as a product.

The carbon monoxide to be fed to the reaction system may be used as a pure gas or may be used as a gas diluted with an inactive gas (e.g., nitrogen, helium, and carbon dioxide). Moreover, exhausted gas component(s) containing carbon monoxide obtained from the succeeding step(s) (e.g., a flash evaporation step, a distillation step, a heat exchanger, and a condenser) may be recycled to the reaction system. The carbon monoxide partial pressure in the reactor may be, for example, about 2 to 30 atmospheres and preferably about 4 to 15 atmospheres, and may be, for example, about 0.8 to 3 MPa, preferably about 1.05 to 2.5 MPa, and more preferably about 1.15 to 2 MPa as an absolute pressure.

In the carbonylation reaction, hydrogen is formed (or generated) by a shift reaction between carbon monoxide and water. Additionally, hydrogen may be fed to the reaction system. The hydrogen may be fed as a mixed gas with carbon monoxide as a raw material to the reaction system. Moreover, the hydrogen may be fed to the reaction system by recycling gaseous component(s) (including hydrogen, carbon monoxide, and others) exhausted in the succeeding distillation step(s) (distillation column), if necessary after suitably purifying the gaseous component(s). The hydrogen partial pressure in the reaction system may be, for example, about 0.5 to 200 kPa, preferably about 1 to 150 kPa, and more preferably about 5 to 100 kPa (e.g., 10 to 70 kPa) as an absolute pressure.

The carbon monoxide partial pressure or hydrogen partial pressure in the reaction system may be adjusted, for example, by suitably adjusting the amount of the carbon monoxide and hydrogen fed and/or recycled to the reaction system, the amount of the offgas in the reactor, the amount of raw substances (e.g., methanol) fed to the reaction system, the reaction temperature, the reaction pressure, and others.

In the carbonylation reaction, the reaction temperature may be, for example, about 150 to 250° C., preferably about 160 to 230° C., and more preferably about 180 to 220° C. Moreover, the reaction pressure (total reactor pressure) may be, for example, about 15 to 40 atmospheres, and the reaction pressure in terms of gauge pressure may be, for example, about 1 to 5 MPa, preferably about 1.5 to 4 MPa, and more preferably about 2 to 3.5 MPa.

The reaction may be carried out in the presence or absence of a solvent. The reaction solvent is not limited to a specific one as long as the reactivity, or the separation or purification efficiency does not decrease, and a variety of solvents may be used. In usual cases, acetic acid as a product may be practically utilized as a solvent.

The concentration of water in the reaction system is not limited to a specific one, and may be a low concentration. The concentration of water in the reaction system is, for example, about 0.1 to 10% by weight, preferably about 0.1 to 6% by weight, and more preferably about 0.1 to 4% by weight in the whole liquid-phase of the reaction system. The solubility of carbon monoxide in the solution fed to the flasher is decreased by carrying out the reaction while maintaining a specified concentration of each component [particularly, an iodide salt (lithium iodide) and water] in the reaction system, and the loss of carbon monoxide can be reduced. In order to reduce the loss of carbon monoxide, it is particularly preferable that the concentration of the iodide salt be 6 to 25% by weight (preferably 7 to 25% by weight) and the concentration of water be 0.1 to 6% by weight (preferably 0.1 to 4% by weight).

In the foregoing carbonylation reaction, production of acetic acid is accompanied by production of an ester of the produced acetic acid with methanol(methyl acetate), water generated with the esterification reaction, additionally acetaldehyde, propionic acid, and others.

In the reaction system, generation of aldehydes may be depressed or inhibited by removing the aldehyde in the recycling stream from the succeeding step(s) (e.g., distillation column), or by modifying the reaction conditions, for example, reducing the proportion of the co-catalyst such as an alkyl iodide and/or the hydrogen partial pressure. Moreover, the generation of hydrogen in the reaction system may be depressed or inhibited by adjusting the water concentration.

The space time yield of the objective acetic acid in the reaction system may be, for example, about 5 mol/Lh to 50 mol/Lh, preferably about 8 mol/Lh to 40 mol/Lh, and more preferably about 10 mol/Lh to 30 mol/Lh.

The gaseous component withdrawn from the upper part (or top) of the reactor for the purpose of the pressure control of the reactor or others is preferably cooled with a condenser, a heat exchanger or other means to remove part of the reaction heat. It is preferable that the cooled gaseous component be separated into a liquid component (containing acetic acid, methyl acetate, methyl iodide, acetaldehyde, water, and others) and a noncondensable component (containing carbon monoxide, hydrogen, and others), the liquid component be recycled to the reactor and the non-condensable component be introduced into the scrubber system.

(Flash Evaporation Step)

In the flash evaporation step (flasher), from the reaction mixture fed from the reaction step, a liquid stream (or a higher boiling point fraction) containing at least a higher boiling point catalyst component (a metal catalyst component, e.g., a rhodium catalyst and an iodide salt) is separated as a liquid (component), and a vaporized stream (or a lower boiling point fraction) (acetic acid stream) containing acetic acid is separated as a vapor (component).

The separation of the rhodium catalyst component may be conducted by a conventional separation method or a conventional separation apparatus, and may usually be carried out with the use of a flash distillation column. Moreover, the rhodium catalyst component may be separated by means of distillation in combination with a mist- or solid-collecting method which is widely used in industrial application.

In the flash evaporation step, the reaction mixture may be separated into the vapor component (or vaporized stream) and the liquid component (or liquid stream) with or without heating. For example, in adiabatic flash, the reaction mixture may be separated into the vapor component and the liquid component without heating and with reduced pressure, and in thermostatic flash, the reaction mixture may be separated into the vapor component and the liquid component with heating and reduced pressure. The reaction mixture may be separated into the vapor component and the liquid component by combining these flash conditions. These flash distillation steps may be carried out, for example, at a temperature of about 80 to 200° C. under a pressure (absolute pressure) of about 50 to 1,000 kPa (e.g., about 100 to 1,000 kPa), preferably about 100 to 500 kPa, and more preferably about 100 to 300 kPa.

The flash evaporation step may be composed of a single step, or may be composed of a plurality of steps in combination. Moreover, a distillation-column-type flasher may be used. The liquid stream containing the higher boiling point catalyst component (rhodium catalyst component) separated by such a step is usually recycled to the reaction system. In the present invention, a heat exchanger may be installed in this recycle line to cool the liquid stream. Cooling of the fraction with the heat exchanger to a temperature of, for example, about 20 to 220° C., preferably about 40 to 200° C., and more preferably about 60 to 180° C. can improve the heat removal efficiency of the whole system.

The vaporized stream (acetic acid stream) separated in the flasher contains a product acetic acid, in addition, a co-catalyst such as hydrogen iodide or methyl iodide, an ester of the product acetic acid with methanol (e.g., methyl acetate), water, a small amount of by-product(s) (e.g., acetaldehyde and propionic acid). The acetic acid stream may be distilled in the first distillation column and the second distillation column to produce a purified acetic acid. In the present invention, since the reaction heat transferred from the reaction solution to the flash vapor can partly be cooled by introducing part of the vaporized stream (acetic acid stream) into a heat exchanger and condensing the introduced stream, the heat removal efficiency can be improved, and acetic acid with a high purity can be produced without installing an external circulation cooling unit in the reactor. The proportion (feed ratio) of the stream to be introduced into the heat exchanger in the vaporized stream separated by the flasher is, for example, about 1 to 50% by weight, preferably about 3 to 45% by weight (e.g., about 4 to 30% by weight), and more preferably about 5 to 25% by weight (particularly about 7 to 20% by weight). In the present invention, the introduction of the vaporized stream into the heat exchanger at such a proportion (particularly, 7 to 20% by weight) allows effective miniaturization of the apparatus without decreasing the reaction efficiency. Further, the vaporized stream may be cooled with the heat exchanger to a temperature of, for example, about 10 to 70° C., preferably about 10 to 50° C., and more preferably about 10 to 30° C. As described above, the loss of carbon monoxide can be inhibited by controlling the concentration of each component in the reaction system and cooling the above-mentioned predetermined amount of the vaporized stream at such a temperature, and the heat removal efficiency can be improved without decreasing the reaction efficiency. As described above, the liquid component in the cooled stream may be recycled to the reactor, or may be purified with the after-mentioned distillation and/or adsorption treatment or others to give acetic acid with a high purity. In order to cool the reactor, it is preferred to recycle the liquid component to the reactor. On the other hand, the gaseous component in the cooled stream is preferably introduced into the scrubber system.

(Distillation Step)

The distillation step is not particularly limited to a specific one as long as the stream vaporized in the above-mentioned evaporation step is fed to the distillation column to distill acetic acid. In the present invention, as described above, since the reaction heat can be removed by condensing part of the vaporized stream with the heat exchanger, the column diameter of the distillation column and the size of the condenser attached to the column can be reduced. Thus, the equipment of the plant is simplified. The distillation step may be a step in which a treatment for removing the lower boiling point component and a treatment for removing water are carried out in a single distillation column (for example, a step utilizing a distillation column described in Japanese Patent No. 3616400 publication) or a step in which a treatment for removing the lower boiling point component and a treatment for removing water in a first distillation column is followed by a further purification step in a second distillation column. Considering the purification efficiency and others, in the preferred distillation step, the treatment for removing the lower boiling point component is mainly carried out in the first distillation column, and the treatment for removing water is mainly carried out in the second distillation column.

(First Distillation Column)

Part of the acetic acid stream (vaporized stream or lower boiling point fraction) fed from the flasher is introduced into the heat exchanger, and the remaining (residual) acetic acid stream is fed to the first distillation column. In the first distillation column, a lower boiling point fraction (or a first overhead fraction) containing at least part of an lower boiling point component (e.g., methyl iodide, methyl acetate, and acetaldehyde) and a higher boiling point fraction (or a first bottom fraction) containing at least part of a higher boiling point component (e.g., propionic acid and water) are separated from the residual acetic acid stream, and a low boiling point fraction (a side stream) containing at least acetic acid is withdrawn by side cut.

As described above, the acetic acid stream fed to the first distillation column is not limited to an acetic acid stream obtained by removing the rhodium catalyst component from the reaction mixture of the reaction system. The acetic acid stream may contain at least acetic acid, hydrogen iodide, the lower boiling point component, the higher boiling point component, and others; or simply may be a mixture of these components. Moreover, the reaction mixture from the reaction system may directly be fed as the acetic acid stream to the first distillation column, and the first bottom fraction containing the rhodium catalyst component may be withdrawn from the bottom of the first distillation column.

As the first distillation column, there may be used, for example, a conventional distillation column, e.g., a plate column, a packed column, and others. Incidentally, the material of the distillation column is not limited to a specific one, and a glass, a metal, a ceramic, or others can be used. In usual, a distillation column made of a metal is used practically.

The distillation temperature and pressure in the first distillation column may suitably be selected depending on the condition such as the species of the distillation column, or the main subject (target) for removal selected from the lower boiling point component and the higher boiling point component. For example, for the plate column, the inner pressure of the column (usually, the pressure of the column top) may be about 0.01 to 1 MPa, preferably about 0.01 to 0.7 MPa, and more preferably about 0.05 to 0.5 MPa in terms of gauge pressure.

Moreover, in the first distillation column, the inner temperature of the column (usually, the temperature of the column top) may be adjusted by adjusting the inner pressure of the column, and may be, for example, about 20 to 180° C., preferably about 50 to 150° C., and more preferably about 100 to 140° C.

Moreover, for the plate column, the theoretical number of plates is not particularly limited to a specific one, and, depending on the species of the component to be separated, is about 5 to 50, preferably about 7 to 35, and more preferably about 8 to 30. Further, in order to separate acetaldehyde highly (or with a high precision) in the first distillation column, the theoretical number of plates may be about 10 to 80, preferably about 20 to 60, and more preferably about 25 to 50.

In the first distillation column, the reflux ratio may be selected from, for example, about 0.5 to 3,000, and preferably about 0.8 to 2,000 depending on the above-mentioned theoretical number of plates, or may be reduced by increasing theoretical number of plates. Incidentally, the lower boiling point fraction obtained by removing the higher boiling point catalyst component from the flash evaporation step is not necessarily subjected to reflux, and may be fed from the top of the first distillation column.

Since the first overhead fraction separated from the first distillation column contains a useful component (e.g., methyl iodide, methyl acetate, and water), the first overhead fraction may be liquefied by a condenser, a heat exchanger, or other means and then recycled to the reactor and/or the first distillation column. In this case, in order to remove the reaction heat in the reactor, the liquid component may be recycled to the reactor. Incidentally, the offgas component (e.g., carbon monoxide and hydrogen) may be removed from the liquid component to recycle the remaining (residual) liquid component. Moreover, among lower boiling point components in the first overhead fraction, acetaldehyde deteriorates the quality of acetic acid as a final product. Thus, if necessary, after removing acetaldehyde (e.g., after removing acetaldehyde by subjecting the fraction containing the lower boiling point impurities to the after-mentioned acetaldehyde separation step (acetaldehyde-separating column)), the remaining component(s) may be recycled to the reaction system and/or the first distillation column. Incidentally, the offgas component may be introduced into the scrubber system.

The first bottom fraction (bottom solution) separated in the first distillation column contains water, acetic acid, an entrained rhodium catalyst, lithium iodide, in addition, acetic acid remaining without being evaporated, the lower boiling point impurities, and others. Thus, if necessary, the first bottom fraction may be recycled to the reaction system and/or the flasher. Incidentally, prior to recycling, propionic acid, which deteriorates the quality of acetic acid as a final product, may be removed off.

(Second Distillation Column)

In the second distillation column, hydrogen iodide, a lower boiling point component, and a higher boiling point component, each of which remains without being separated, in the first distillation column are removed with further high precision. As the second distillation column, there may be used a conventional distillation column, for example, a plate column, a packed column, and other columns. Moreover, the inner temperature of the column, the inner pressure of the column, the theoretical number of plates, and the reflux ratio in the second distillation column may be selected depending on the species of the distillation column, for example, may be selected from the same (similar) range with the range of the above first distillation column.

Since the second overhead fraction separated from the second distillation column contains a useful component such as water, methyl iodide, or methyl acetate, the second overhead fraction may directly be recycled to the reactor and/or the second distillation column. Moreover, since the second overhead fraction contains acetaldehyde, the second overhead fraction, for example, may be recycled after removing acetaldehyde with the after-mentioned aldehyde-separating column, if necessary. Incidentally, the offgas component may be introduced into the scrubber system.

Further, the second bottom fraction may be discharged from the bottom or lower part of the column. Since the second bottom fraction separated from the second distillation column is rich in propionic acid, an aldehyde compound, an acetate ester compound, an alkyl iodide compound, a metal iodide compound, and others, the second bottom fraction may directly be discarded (or removed off). Incidentally, since the second bottom fraction further contains water or acetic acid, if necessary, the second bottom fraction from which propionic acid is removed and/or recovered may be recycled to the reaction system.

In the second distillation column, the purified acetic acid stream is withdrawn by side cut. The position of the side stream port may usually be at a middle or lower part of the distillation column. Incidentally, by withdrawing the acetic acid stream from the side stream port existing at an upper position relative to the bottom port for withdrawing the second bottom fraction, the side stream and the second bottom fraction may efficiently be separated.

(Iodide-Removing Step)

The purified acetic acid recovered by side cut from the second distillation column is usually introduced into a column for a product acetic acid and obtained as a product acetic acid. Prior to introduction into the column for a product acetic acid, the purified acetic acid may further be subjected to an iodide-removing step to remove an iodide (e.g., a $C_{1-15}$alkyl iodide such as hexyl iodide or decyl iodide).

In the iodide-removing step, the acetic acid stream may be contacted with a remover (removing agent or material) having an iodide-removability or iodide-adsorbability (e.g., a zeolite, an activated carbon, and an ion exchange resin). In order to efficiently remove the iodide from the acetic acid stream which is continuously obtained (in a continuous system), an ion exchange resin having iodide-removability or iodide-adsorbability, particularly an iodide-removing column provided with the ion exchange resin therein is advantageously used.

The ion exchange resin to be used is usually an ion exchange resin (usually a cation exchange resin) in which at least part of the active site (e.g., usually an acidic group such as a sulfone group, a carboxyl group, a phenolic hydroxyl group, or a phosphone group) is substituted or exchanged with a metal. The metal may include, for example, at least one member selected from the group consisting of silver (Ag), mercury (Hg), and cupper (Cu). The cation exchange resin as a base (substrate) may be any one of a strong acidic cation exchange resin and a weak (mild) acidic cation exchange resin, and the preferred one includes a strong acidic cation exchange resin, for example, a macroreticular ion exchange resin, and the like.

In the ion exchange resin, the proportion of the active site exchanged to the metal (or substituted with the metal) may be, for example, about 10 to 80% by mol, preferably about 25 to 75% by mol, and more preferably about 30 to 70% by mol.

At least contacting of the acetic acid stream from the second distillation column with the ion exchange resin (preferably passing of the acetic acid stream through the ion exchange resin) achieves removal of the iodide. While contacting with (or passing through) the ion exchange resin, if necessary, the temperature of the acetic acid stream may be increased (or elevated) stepwise. The stepwise temperature elevation ensures to inhibit outflow or effusion of the metal from the ion exchange resin, as well as to remove the iodide efficiently.

Examples of the iodide-removing column may include a packed column packing inside thereof at least the ion exchange resin which is exchanged with a metal, a column provided with a bed of an ion exchange resin (e.g., a bed comprising a particulate resin) (a guard bed) and the like. The iodide-removing column may be provided with the metal-exchanged ion exchange resin, and in addition, another ion exchange resin (e.g., a cation exchange resin, an anion exchange resin, and a nonion exchange resin) inside thereof. Even when the metal is effused from the metal-exchanged ion exchange resin, arrangement of the cation exchange resin at the downstream side of the metal-exchanged ion exchange resin (e.g., arrangement of the cation exchange resin by packing, or arrangement of the cation exchange resin as a resin bed) allows the effused metal to be captured with the cation exchange resin and be removed from the acetic acid stream.

The temperature of the iodide-removing column may be, for example, about 18 to 100° C., preferably about 30 to 70° C., and more preferably about 40 to 60° C.

The rate of the acetic acid stream to be passed through is not limited to a specific one, and may be, for example, in an iodide-removing column utilizing a guard bed, e.g., about 3 to 15 BV/h (bed volume per hour), preferably about 5 to 12 BV/h, and more preferably about 6 to 10 BV/h.

In the iodide-removing step, the acetic acid stream may be at least contacted with the metal-exchanged ion exchange resin. For example, the iodide-removing column may comprise a column provided with the metal-exchanged ion exchange resin and a column provided with another ion exchange resin. For example, the iodide-removing column may comprise an anion exchange resin column, and a metal-exchanged ion exchange resin column on the downstream side of the anion exchange resin column, or may comprise a metal-exchanged ion exchange resin column, and a cation exchange resin column on the downstream side of the metal-exchanged ion exchange resin column. The details of the former example can be referred by WO02/062740, and others.

(Acetaldehyde-Separating Step)

When the fraction containing acetaldehyde generated by the reaction is recycled and circulated to the reaction system, the distillation column(s), and others, the amount of by-product(s) such as propionic acid, an unsaturated aldehyde, or an alkyl iodide increases. Thus, it is preferred to remove acetaldehyde in the solution to be recycled to the reaction system and/or the distillation column. The method for separating acetaldehyde may comprise feeding a recycle solution (a solution to be recycled) to the acetaldehyde-separating column to separate a lower boiling point fraction containing acetaldehyde and a higher boiling point fraction containing methyl iodide, methyl acetate, water, and others, and then separating acetaldehyde from the top or upper part of the aldehyde-separating column, with the offgas component (e.g., carbon monoxide and hydrogen). Further, the offgas component may be previously removed off with a condenser or a cooling unit, prior to the separation of acetaldehyde. Furthermore, since the higher boiling point fraction obtained by removing acetaldehyde as the lower boiling point fraction contains methyl iodide, water, methyl acetate, acetic acid, and the like, the higher boiling point fraction may be recycled to the reaction system.

As the aldehyde-separating column, for example, there may be used a conventional distillation column, e.g., a plate column, a packed column, a flash distillation column, and others.

The temperature (the temperature of the column top) and the pressure (the pressure of the column top)) in the acetaldehyde-separating column may be selected depending on the respective quantities and quantitative ratio of acetaldehyde and methyl iodide as well as the species of the distillation column, and is not particularly limited to a specific one as long as at least acetaldehyde is separable as a lower boiling point fraction from the overhead fraction(s) obtained in the first and/or second distillation column(s) by utilizing difference between acetaldehyde and other components (particularly methyl iodide) in boiling point. For example, for the plate column, the pressure of the column top is about 10 to 1,000 kPa, preferably about 10 to 700 kPa, and more preferably about 100 to 500 kPa as an absolute pressure. The inner temperature of the column (the temperature of the column top) is, for example, about 10 to 80° C., preferably about 20 to 70° C., and more preferably about 40 to 60° C. Theoretical number of plates may be, for example, about 5 to 80, preferably about 8 to 60, and more preferably about 10 to 50.

In the acetaldehyde-separating column, the reflux ratio may be selected from about 1 to 1000, preferably about 10 to 800, and preferably about 50 to 600 (e.g., about 100 to 600) depending on the above-mentioned theoretical number of plates. Moreover, the lower boiling point fraction containing acetaldehyde contains some methyl iodide, and acetaldehyde and methyl iodide may further be separated through an additional step, for example, a water extraction step or a distillation step.

EXAMPLES

The following examples are intended to describe this invention in further detail and should by no means be interpreted as defining the scope of the invention.

Comparative Example 1

As a plant for producing acetic acid at an operating time of 8000 hours per year and an annual output of 500,000 t, the following experiments were performed. The plant shown in the diagram of FIG. 1 was operated without using a heat exchanger E3 for cooling a higher boiling point fraction separated in a flasher V2 and without using a heat exchanger E4 for cooling part of a lower boiling point fraction separated in the flasher V2 and a line for the heat exchanger E4. As the reaction conditions, the reaction pressure was 2.76 MPaG (gauge pressure), the reaction temperature was 185° C., and the carbon monoxide partial pressure was 1.06 MPaA (absolute pressure). The operation was continuously conducted while maintaining the concentration of each component in the reaction solution at water of 8% by weight, methyl acetate of 2% by weight, methyl iodide of 13% by weight, lithium iodide of 13% by weight, and rhodium of 600 ppm. The quantity of the generated reaction heat was $3.4 \times 10^7$ kcal/hour. In this plant, the reaction heat was removed by using a condenser E1 attached to a reactor V1 and a condenser E2 attached to a first distillation column T1.

Example 1

The plant shown in the diagram of FIG. 1 was continuously operated in the same manner as in Comparative Example 1. Specifically, the reaction heat was removed by using the condenser E1, the condenser E2, the heat exchanger E3, and the heat exchanger E4. The yield and purity of the resulting acetic acid in Example 1 ware almost the same as those in Comparative Example 1.

The balance of the heat quantity in the plant of Comparative Example 1 and that in the plant of Example 1 were compared. The results are shown in Table 1.

TABLE 1

| Balance of Heat Quantity [unit: kcal/hour] | | | | | |
|---|---|---|---|---|---|
| | E1 | E2 | E3 | E4 | Total quantity |
| Com. Ex. 1 | $1.9 \times 10^5$ | $3.4 \times 10^7$ | — | — | $3.4 \times 10^7$ |
| Ex. 1 | $1.9 \times 10^5$ | $2.0 \times 10^7$ | $7.1 \times 10^6$ | $6.3 \times 10^6$ | $3.4 \times 10^7$ |

Moreover, assuming that the feed amount (t/hour) of the condenser E1 in Comparative Example 1 was 1, the feed amount of the first distillation column T1, that of the heat exchanger E3, and that of the heat exchanger E4 were expressed as relative values. The results are shown in Table 2.

TABLE 2

| Feed Amount | | | | |
|---|---|---|---|---|
| | E1 | T1 | E3 | E4 |
| Com. Ex. 1 | 1 | 115 | — | — |
| Ex. 1 | 1 | 69 | 191 | 21 |

Further, assuming that the cost of equipment (unit: one hundred million yen) of the condenser E2 in Comparative Example 1 was 1, the cost of equipment of the condenser E3, that of the condenser E4, that of the flasher V2, that of the first distillation column T1, and that of the second distillation column T2 were expressed as relative values. The results are shown in Table 3. Incidentally, the cost of equipment of the condenser E1 was omitted because of no difference between Comparative Example 1 and Example 1.

TABLE 3

Cost of Equipment

|  | E2 | E3 | E4 | V2 | T1 | T2 | Total cost of E2 to T1 |
|---|---|---|---|---|---|---|---|
| Com. Ex. 1 | 1 | — | — | 0.48 | 0.78 | 1.11 | 2.26 |
| Ex. 1 | 0.63 | 0.20 | 0.26 | 0.39 | 0.66 | 1.11 | 2.14 |

As shown in the results of Table 3, the cost of equipment of Example 1 is 6.2% (about 140 million yen) lower than that of Comparative Example 1. That is, use of the heat exchanger E3, the heat exchanger E4 and a line therefor miniaturizes the flasher V2, the first distillation column T1, and the condenser E2, and the cost of equipment is reduced.

Comparative Example 2

As a plant for producing acetic acid at an operating time of 8000 hours per year and an annual output of 500,000 t, the following experiments were performed. The plant shown in the diagram of FIG. 1 was operated without using the heat exchanger E4 and a line for the heat exchanger E4. As the reaction conditions, the reaction pressure was 2.76 MPaG (gauge pressure), the reaction temperature was 185° C., and the carbon monoxide partial pressure was 1.06 MPaA (absolute pressure). The operation was continuously conducted while maintaining the concentration of each component in the reaction solution at water of 8% by weight, methyl acetate of 2% by weight, methyl iodide of 13% by weight, lithium iodide of 13% by weight, and rhodium of 600 ppm. The quantity of the generated reaction heat was $3.4 \times 10^7$ kcal/hour. In this plant, the reaction heat was removed by using the condenser E1, the condenser E2, and the heat exchanger E3.

Example 2

The plant shown in the diagram of FIG. 1 was continuously operated in the same manner as in Comparative Example 2. Specifically, the reaction heat was removed by using the condenser E1, the condenser E2, the heat exchanger E3, and the heat exchanger E4. Incidentally, as described later, Example 2 is different in feed amount from Example 1. The yield and purity of the resulting acetic acid in Example 2 ware almost the same as those in Comparative Example 2.

The balance of the heat quantity in the plant of Comparative Example 2 and that in the plant of Example 2 were compared. The results are shown in Table 4.

TABLE 4

Balance of Heat Quantity [unit: kcal/hour]

|  | E1 | E2 | E3 | E4 | Total quantity |
|---|---|---|---|---|---|
| Com. Ex. 2 | $1.9 \times 10^5$ | $2.2 \times 10^7$ | $1.2 \times 10^7$ | — | $3.4 \times 10^7$ |
| Ex. 2 | $1.9 \times 10^5$ | $2.0 \times 10^7$ | $1.2 \times 10^7$ | $2.5 \times 10^6$ | $3.4 \times 10^7$ |

Moreover, assuming that the feed amount (t/hour) of the condenser E1 in Comparative Example 1 was 1, the feed amount of the first distillation column T1, that of the heat exchanger E3, that of the heat exchanger E4, and that of the second distillation column T2 were expressed as relative values. The results are shown in Table 5.

TABLE 5

Feed Amount

|  | E1 | T1 | E3 | E4 | T2 |
|---|---|---|---|---|---|
| Com. Ex. 2 | 1 | 75 | 172 | — | 40 |
| Ex. 2 | 1 | 68 | 172 | 8 | 36 |

Further, assuming that the cost of equipment (unit: one hundred million yen) of the condenser E2 in Comparative Example 1 was 1, the cost of equipment of the condenser E2, that of the condenser E3, that of the condenser E4, that of the flasher V2, that of the first distillation column T1, and that of the second distillation column T2 were expressed as relative values. The results are shown in Table 6. Incidentally, the cost of equipment of the condenser E1 was omitted because of no difference between Comparative Example 2 and Example 2.

TABLE 6

Cost of Equipment

|  | E2 | E3 | E4 | V2 | T1 | T2 | Total cost of E2 to T1 | Total cost of E2 to T2 |
|---|---|---|---|---|---|---|---|---|
| Com. Ex. 2 | 0.65 | 0.34 | — | 0.42 | 0.72 | 1.03 | 2.13 | 3.16 |
| Ex. 2 | 0.59 | 0.34 | 0.10 | 0.38 | 0.65 | 0.93 | 2.06 | 2.99 |

As shown in the results of Table 6, the cost of equipment of Example 2 is 8.8% lower than that of Comparative Example 1 and 5.4% lower than that of Comparative Example 2. That is, use of the heat exchanger E4 and a line therefor miniaturizes the flasher V2, the first distillation column T1, the condenser E2, and the second distillation column T2, and the cost of equipment is reduced.

Comparative Example 3

As a plant for producing acetic acid at an operating time of 8000 hours per year and an annual output of 500,000 t, the following experiments were performed. The plant shown in the diagram of FIG. 1 was operated by installing an external circulation cooling unit E6 in the reactor in place of the heat exchanger E4 and a line therefor. As the reaction conditions, the reaction pressure was 2.76 MPaG (gauge pressure), the reaction temperature was 185° C., and the carbon monoxide partial pressure was 1.15 MPaA (absolute pressure). The operation was continuously conducted while maintaining the concentration of each component in the reaction solution at water of 2.5% by weight, methyl acetate of 3% by weight, methyl iodide of 9% by weight, lithium iodide of 15% by weight, and rhodium of 900 ppm. The quantity of the generated reaction heat was $3.4 \times 10^7$ kcal/hour. In this plant, the reaction heat was removed by using the condenser E1, the condenser E2, the heat exchanger E3, the external circulation cooling unit E6.

Example 3

The plant shown in the diagram of FIG. 1 was continuously operated in the same manner as in Comparative Example 3. Specifically, the reaction heat was removed by using the condenser E1, the condenser E2, the heat exchanger E3, and the heat exchanger E4. The yield and purity of the resulting acetic acid in Example 3 ware almost the same as those in Comparative Example 3.

The balance of the heat quantity in the plant of Comparative Example 3 and that in the plant of Example 3 were compared. The results are shown in Table 7.

TABLE 7

Balance of Heat Quantity [unit: kcal/hour]

|  | E1 | E2 | E3 | E4 | E6 | Total quantity |
|---|---|---|---|---|---|---|
| Com. Ex. 3 | $6.2 \times 10^5$ | $1.1 \times 10^7$ | $0.6 \times 10^7$ | — | $1.6 \times 10^7$ | $3.4 \times 10^7$ |
| Ex. 3 | $6.2 \times 10^5$ | $1.1 \times 10^7$ | $1.0 \times 10^7$ | $1.2 \times 10^7$ | — | $3.4 \times 10^7$ |

Moreover, assuming that the feed amount (t/hour) of the condenser E1 in Comparative Example 1 was 1, the feed amount of the first distillation column T1, that of the heat exchanger E3, that of the heat exchanger E4, that of the second distillation column T2, and that of the external circulation cooling unit were expressed as relative values. The results are shown in Table 8.

TABLE 8

Feed Amount

|  | E1 | T1 | E3 | E4 | E6 | T2 |
|---|---|---|---|---|---|---|
| Com. Ex. 3 | 3 | 54 | 149 | — | 155 | 32 |
| Ex. 3 | 3 | 54 | 253 | 38 | — | 32 |

From the results of Table 8, although the feed amount to the heat exchanger E3 in Example 3 is larger than that of Comparative Example 3, the difference between both feed amounts is smaller than the feed amount of the external circulation cooling unit E6.

Further, assuming that the cost of equipment (unit: one hundred million yen) of the condenser E2 in Comparative Example 1 was 1, the cost of equipment of the condenser E2, that of the condenser E3, that of the condenser E4, that of the external circulation cooling unit E6, that of the flasher V2, that of the first distillation column T1, and that of the second distillation column T2 were expressed as relative values. The results are shown in Table 9. Incidentally, the cost of equipment of the condenser E1 was omitted because of no difference between Comparative Example 3 and Example 3.

TABLE 9

Cost of Equipment

|  | E2 | E3 | E4 | E6 | V2 | T1 | T2 | Total cost of E2 to T1 | Total cost of E2 to T2 |
|---|---|---|---|---|---|---|---|---|---|
| Com. Ex. 3 | 0.46 | 0.21 | — | 0.81 | 0.21 | 0.80 | 0.78 | 2.49 | 3.27 |
| Ex. 3 | 0.46 | 0.37 | 0.56 | — | 0.30 | 0.80 | 0.78 | 2.49 | 3.27 |

From the results of Table 9, the cost of equipment in Comparative Example 3 is equal to that in Example 3. Further, the loss amount of carbon monoxide, the amount of vapor and cooled water, and the proportional cost of the total of these amounts were estimated. The results are shown in Table 10. Incidentally, for comparison, Comparative Example 4 was conducted and estimated in the same manner as in Comparative Example 3 except that the concentration of water was 8% by weight, the concentration of methyl acetate was 1.6% by weight, the concentration of methyl iodide was 13% by weight, the concentration of lithium iodide was 5% by weight, and the concentration of rhodium was 600 ppm.

TABLE 10

| | Proportional Cost | | | | |
|---|---|---|---|---|---|
|  | CO loss | Vapor and cooled water | Total amount of CO loss and vapor and cooled water | Concentration of water | Concentration of LiI |
| Com. Ex. 3 | 1 | 1 | 1 | 2.5 | 15 |
| Com. Ex. 4 | 2.2 | — | — | 8 | 5 |
| Ex. 3 | 1.7 | 1 | 1.3 | 2.5 | 15 |

From the results of Table 10, the solubility of carbon monoxide to be fed to the flasher is lowered by decreasing the water content and increasing the lithium iodide concentration in the reaction solution, and the loss of carbon monoxide is inhibited. However, Comparative Examples 3 and 4 using the external circulation cooling unit are sometimes impossible of operation due to sedimentation of rhodium. Moreover, considering the loss of rhodium, the proportional cost of Example 3 is significantly lower than that of Comparative Example 3.

INDUSTRIAL APPLICABILITY

The production process of the present invention relates to an industrial production process of acetic acid, particularly a continuous production process of acetic acid in a large-sized plant, and is useful for obtaining a highly purified acetic acid in a resource-saving and energy-saving equipment.

DESCRIPTION OF REFERENCE NUMERALS

1 Reactor
2 Flasher
3 First distillation column
4 Second distillation column
5, 8, 9 Condenser
6, 7 Heat exchanger

The invention claimed is:
1. A process for producing acetic acid, which comprises
a reaction step for continuously allowing at least one member selected from the group consisting of methanol, dimethyl ether, and methyl acetate to react with carbon monoxide in a catalyst system comprising a rhodium catalyst, an iodide salt, and methyl iodide in the presence of acetic acid and water in a reactor,
a flash evaporation step for continuously feeding a flasher with a liquid reaction medium withdrawn from the reactor to separate a liquid stream and a vaporized stream from the liquid reaction medium, and
a distillation step for feeding a distillation column with the vaporized stream for obtaining a purified acetic acid,
wherein part of the vaporized stream is introduced into a heat exchanger for condensation, and a liquefied stream condensed by the heat exchanger is recycled to the reactor.
2. A process according to claim 1, wherein 1 to 50% by weight of the vaporized stream is introduced into the heat exchanger.
3. A process according to any one of claim 1 or 2, wherein an acetic acid stream obtained from the distillation step for purifying acetic acid is subjected to a further distillation and/or an adsorption treatment for obtaining a further purified acetic acid.

4. A process according to claim 1, wherein the liquid stream separated by the flasher is introduced into the heat exchanger and cooled, and then the cooled stream is recycled to the reactor.

5. A process according to claim 1, wherein each of a gaseous component from the reactor and an overhead fraction from the distillation column is condensed by a condenser.

6. A process according to claim 1, wherein the reactor is a reactor without a heat-removable or cooling unit.

7. A process according to claim 1, wherein, in the reaction step, the reaction is conducted while maintaining the reaction system at concentrations of the iodide salt of 2 to 25% by weight, methyl iodide of 1 to 20% by weight, methyl acetate of 0.1 to 30% by weight, and water of 0.1 to 10% by weight in a whole liquid phase of the reaction system.

8. A process according to claim 7, wherein the concentration of the iodide salt is 6 to 25% by weight, and the concentration of water is 0.1 to 6% by weight.

9. A method for controlling a temperature in a production process of acetic acid, which comprises a reaction step for continuously allowing at least one member selected from the group consisting of methanol, dimethyl ether, and methyl acetate to react with carbon monoxide in a catalyst system comprising a rhodium catalyst, an iodide salt, and methyl iodide in the presence of acetic acid and water, a flash evaporation step for continuously withdrawing a liquid reaction medium from the reaction step to separate a liquid stream and a vaporized stream from the liquid reaction medium, and a distillation step for distilling the vaporized stream for obtaining a purified acetic acid, wherein part of the vaporized stream is introduced into a heat exchanger for condensation, and a liquefied stream condensed by the heat exchanger is recycled to the reaction step.

10. A process according to claim 2, wherein a residual part of the vaporized stream is introduced into the distillation step.

* * * * *